United States Patent [19]

Asano et al.

[11] Patent Number: 4,568,540

[45] Date of Patent: Feb. 4, 1986

[54] ORAL HYGIENE COMPOSITIONS

[75] Inventors: Akira Asano, Princeton; Maria C. Gaffar, Somerset, both of N.J.

[73] Assignee: Johnson & Johnson, New Brunswick, N.J.

[21] Appl. No.: 601,765

[22] Filed: Apr. 18, 1984

[51] Int. Cl.[4] .......................... A61K 7/16; A61K 7/18; A61K 7/24

[52] U.S. Cl. ....................................... 424/52; 424/151

[58] Field of Search .................................. 424/49–58, 424/151

[56] References Cited

U.S. PATENT DOCUMENTS

| | | | |
|---|---|---|---|
| 4,138,477 | 2/1979 | Gaffar | 424/52 |
| 4,144,323 | 3/1979 | Lamberti | 424/49 |
| 4,146,607 | 3/1979 | Ritchey | 424/54 |
| 4,213,961 | 7/1980 | Curtis et al. | 424/54 |
| 4,256,731 | 3/1981 | Curtis et al. | 424/54 |
| 4,289,754 | 9/1981 | Dhabhar et al. | 424/52 |
| 4,289,755 | 9/1981 | Dhabhar | 424/52 |
| 4,339,432 | 7/1982 | Ritchey et al. | 424/54 |
| 4,416,867 | 11/1983 | Ritchey et al. | 424/49 |
| 4,425,325 | 1/1984 | Ritchey et al. | 424/49 |
| 4,469,674 | 9/1984 | Shah et al. | 424/52 |

Primary Examiner—Shep K. Rose
Attorney, Agent, or Firm—Steven P. Berman

[57] ABSTRACT

An oral hygiene composition containing an effective concentration of a pharmaceutically acceptable fluoride salt, a pharmaceutically acceptable zinc salt, a specific buffering agent, a suitable vehicle and having a pH of from about 3.5 to 6.0.

11 Claims, No Drawings

ORAL HYGIENE COMPOSITIONS

BACKGROUND OF THE INVENTION

The present invention relates to oral hygiene compositions. More particularly, the present invention relates to oral hygiene compositions which prevent and control mouth odor, calculus, plaque and caries and contain active zinc ions and fluoride ions. These compositions are also effective at preventing gingivitis and periodontal disease.

The use of soluble fluoride salts, such as stannous fluoride, sodium monofluorophosphate and sodium fluoride, to reduce the incidence of dental caries in the general population is a well-known and ongoing endeavor. The administration of these fluoride compounds takes many forms, including the fluoridation of drinking water, professional treatment by dentists and incorporation in oral hygiene compositions such as dentifrices and mouthrinses.

It is also known that zinc plays a role in dental care. For example, in U.S. Pat. No. 4,160,821 issued July 10, 1979, there is disclosed a composition for treating gingivitis comprising a vehicle containing a high concentration of glycerol and a zinc salt, such as zinc chloride, that is soluble in the glycerol.

In an article entitled "Inhibition of Plaque Growth by Zinc Salts," Journal of Periodontal Research, Vol. 18, pp. 634–642, 1983, Harrap et al. reported that solutions of zinc salts reduced plaque by 30% along the gingival margin. In "Effect of Some Polyvalent Cations of Plaque Formation In Vivo", Scandinavian Journal of Dental Research Vol. 186, pp. 103-107, 1978, it is indicated that mouthrinses containing either $ZnCl_2$ $AlCl_3$, $MgCl_2$, $SnF_2$ or $SnCl_2$ exhibited significant plaque reducing activity. An oral rinse containing 1.0% zinc salts (as the phenolsulphonate) or 0.125% zinc complex with tribromsalan was found clinically to reduce mean calculus scores by about 60% and 53% respectively, in two consecutive three-month trials as reported by Picozzi et al. in an article entitled, "Calculus Inhibition in Humans", Journal of Periodontology, Volume 43, pp. 692–695, 1972. Zinc compounds (as 1% zinc phenolsulfonate and 0.125% zinc tribromsalan) formulated in an aqueous mouthwash significantly delayed the development of gingivitis in a test group compared to a placebo by Fischman et al., Journal Periodontology, Vol. 44, pp. 535–539, 1975.

In British Patent Specification No. 1,373,003, published Nov. 6, 1974, there is disclosed a dentifrice composition having activity against plaque and calculus on a tooth surface comprising a sparingly soluble zinc salt which is defined as a zinc salt of an acid, other than zinc fluoride or its hydrates, having a water solubility greater than that of zinc phosphate and less than 1 gram of zinc per 100 ml of water at 20° C. and a mixture of detergents. The dentifrice may also contain a compatible abrasive such as alumina and other conventional toothpaste ingredients. U.S. Pat. No. 4,146,606, issued Mar. 27, 1979, relates to a pharmaceutical composition for dental use that can, inter alia, suppress dental caries, this composition comprising a strontium compound, a zinc compound, tannin and, optionally, a fluorine compound.

U.S. Pat. No. 4,138,477, issued Feb. 6, 1979, discloses a composition to prevent and control mouth odor, which is also said to be effective in preventing calculus, plaque, caries and periodontal disease, containing as the essential agent a zinc-polymer complex formed by the reaction or chelation of a zinc compound with an anionic polymer containing carboxylic, sulfonic and/or phosphoric acid radicals. The composition may also include, inter alia, a fluorine-containing compound that protects the teeth against decay. U.S. Pat. No. 4,396,599 issued Aug. 2, 1983, describes anticaries compositions including dentifrices containing a fluoride compound and a zinc compound with a ratio of zinc ion to fluoride ion of at least about 7:1 by weight.

SUMMARY OF THE INVENTION

It is an object of this invention to provide improved oral hygiene compositions.

It is another object of this invention to provide oral hygiene compositions which prevent and control mouth odor, calculus, plaque, caries, and gingivitis.

It is a further object of this invention to provide oral hygiene compositions which minimize astringent taste and exhibit good fluoride and zinc ion bioavailability.

Other objects of this invention will be set forth in, or be apparent from the following detailed description of the invention.

The foregoing objects and other features and advantages of the present invention are achieved by oral hygiene compositions formulated to provide available fluoride and zinc ions from pharmaceutically acceptable salts in a formulation containing a specific buffering system and having a pH of from about 3.5 to 6.0.

DETAILED DESCRIPTION OF THE INVENTION

The present invention relates to oral hygiene compositions containing an effective concentration of a pharmaceutically acceptable fluoride salt and a pharmaceutically acceptable zinc salt, a specific buffering agent and having a pH of from about 3.5 to 6.0.

Typical pharmaceutically acceptable fluoride compounds that are suitable for use in the compositions of this invention include sodium fluoride, potassium fluoride, lithium fluoride, aluminum fluoride, zinc fluoride, stannous fluoride, sodium monofluorophosphate, acidulated phosphate fluoride, ammonium fluoride, ammonium bifluoride, titanium tetrafluoride and amine fluoride.

Zinc salts that are suitable for use in the compositions of this invention include zinc chloride, zinc sulfate, zinc citrate, zinc acetate, zinc lactate, zinc salicylate, zinc thiocyanate, and, more generally, any pharmaceutically acceptable zinc salts.

The fluoride ion concentration can be from as low as 0.0025% to about 4.0% by weight. The preferred range of fluoride ion concentration is about 0.005% to about 1.0% by weight, more preferably about 0.01% to 0.5%. The zinc ion concentration should be from about 0.02% to 30.0% by weight, preferably from about 0.05% to 10.0% and more preferably from about 0.1% to 5.0%. While higher concentrations of both zinc and fluoride ions could be used, no particular advantage would be afforded thereby, and there are some contraindications in the literature concerning the safety of higher concentrations of fluoride and zinc ions.

The ratio of zinc ions to fluoride ions can range from 0.05:1 to 25:1, preferably from about 5:1 to 15:1. The fluoride ions are taken up by the dental enamel and render the teeth less susceptible to caries attack and dental decay by increasing the hardness of the enamel or reducing the enamel solubility. The zinc ions help to prevent the formation of tartar, oral malodor and gingivitis.

The choice of specific buffering agents is essential to the performance of the compositions of the present invention and are required to maintain the acid pH and prevent precipitation of the zinc ion. Sodium gluconate in an amount of from about 0.01 to 10.0%, preferably about 0.05 to 5.0% is a preferred buffering agent. Other organic acids/salts which can be utilized include maleic acid, aspartic acid, gluconic acid, succinic acid, glucuronic acid, glucuronic acid lactone, sodium glutamate and fumaric acid. Other organic acids and salts such as lactic acid, adipic acid and tartaric acid which would be expected to perform in the same manner have proved to be unsatisfactory.

In order to achieve the desired results of the compositions of the present invention, the pH should be maintained between 3.5 and 6.0. This permits the fluoride ions and zinc ions to remain in solution and not precipitate out thereby permitting them to have their desired effect. This can best be achieved by adjusting the pH to the desired range by the addition of a combination of acid saccharin and sodium saccharin in an amount of from about 0.01 to 5.0%, preferably 0.1 to 2.0%. If the sodium salt or acid is utilized alone, the pH can be adjusted by the addition of an appropriate acid or base. The sodium saccharin and saccharin should be in a ratio of from about 20:1 to 2:1, preferably about 7:1.

Suitable pharmaceutically acceptable oral hygiene vehicles that may be used alone or in combination in the compositions of the present invention include glycerol, water, ethanol, polyethylene glycol, propylene glycol, sorbitol and the like. Other vehicles may be used if compatible with the other ingredients in the compositions.

If the compositions of the present invention are in the form of a dentifrice, they should also contain a suitable abrasive. The abrasive should be such that it does not harm the enamel or dentin while being capable of cleaning and polishing the teeth as well as being compatible with the fluoride ions and zinc ions. Preferred abrasives include the silica abrasives. Silica abrasives which are useful are those having an average particle size of from about 0.1 to 45 microns, preferably from about 4 to 20 microns; having a pH from about 3.5 to 9.0; and are usually in the form of precipitated silica, silica xerogels or silica hydrogels. The preferred silica abrasives are the silica hydrogels available from W. R. Grace under the tradename "Hydrous Silica Gel". The preferred silica hydrogels have a water content of 15-60% and a pH of about 4.5. The low pH of the silicas helps to keep the fluoride ions and zinc ions soluble and therefore available and also helps in keeping the pH of the formulations stable. Other suitable silica abrasives include the silica xerogels described in U.S. Pat. No. 4,100,269 and the precipitated silica materials described in U.S. Pat. No. 3,862,307 available from Huber Corporation under the tradename "Zeodent".

The silica abrasives should be present in the dentifrice compositions from about 5.0 to 70.0%, preferably about 10.0 to 40.0%. These materials are compatible with the zinc and fluoride ions in such formulations and serve as cleaning and polishing agents.

The dentifrice formulations should also contain specific polymers which are useful as binders and thickeners in the compositions. These include the non-ionic water-soluble polymers which are compatible with the other ingredients in the formulation. Hydroxyethylcellulose polymers are available from Hercules Inc. under the tradename "Natrosol" and have been found to be preferred in the compositions for maintaining viscosity over a wide pH range. These non-ionic polymers should be present in the compositions in an amount of from about 0.03 to 10.0%, preferably from about 0.1 to 3.0%.

It is often desirable for formulation purposes to use more than one binder to achieve the desired results. In addition to hydroxyalkylcellulosic binders, other binders can be selected from xanthan gum, carrageenan, gum karaya, gum arabic and gum tragacanth. Xanthan gum is preferred and can be utilized in an amount of from about 0.02 to 5.0%, preferably 0.1 to 3.0%.

Another component in dentifrice compositions is a humectant. The humectant serves to keep the dentifrice compositions from hardening upon exposure to air and also imparts a desirable sweetness to the formulations to minimize the astringency ascribed to the zinc chloride. The humectant, on a pure humectant basis, generally comprises from about 5.0 to 80.0%, preferably from about 8.0 to 50.0% by weight of the total compositions. Suitable humectants include edible polyhydric alcohols such as glycerine, sorbitol, xylitol and propylene glycol. Mixtures of glycerine and sorbitol are especially preferred.

Water is another essential component of dentifrice compositions. Water employed in the preparation of commercially suitable dentifrices should preferably be deionized and free of impurities. Water comprises from about 0.05 to 70.0%, preferably from about 15.0 to 50.0% by weight of the formulations. These amounts of water include the free water which is added plus that which is introduced with other materials.

Another ingredient of dentifrice compositions is a suitable surface-active agent or detergent. Suitable surface-active agents are those that are reasonably stable, foam through the pH range and are compatible with the zinc and fluoride compounds as well as the other components. These agents are usually water-soluble, organic compounds and may be anionic, nonionic or cationic in nature. Such materials are well-known and include, for example, the water-soluble salts of high fatty acid monoglyceride monosulfates such as sodium coconut acid monoglyceride monosulfate; higher alkyl sulfates such as sodium lauryl sulfate, alkyl aryl sulfonate such as sodium dodecyl benzene sulfonate, higher fatty acid esters of 1,2-dihydroxypropane sulfonate, and sodium salts of the coconut fatty acid amide of N-methyltaurine. The latter is particularly preferred since it has been found to minimize the astringency of zinc chloride. Particularly useful are the nonionic block copolymers derived from the condensation of polyethylene glycol and polypropylene glycol. These block copolymers are available from Wyandotte Chemical Corp. under the tradename "Pluronic". These block copolymers are available in liquid, paste or solid form. The preferred nonionic block copolymers are the solid materials such as Pluronic F-85, Pluronic F-108 and Pluronic F-127.

Another preferred nonionic detergent is the cogeneric mixture of conjugated polyoxybutylene-polyoxyethylene described in U.S. Pat. No. 4,323,552 sold under the tradename "Butronic" by BASF Wyandotte Corporation. Butronic Polyol L-1 and Butronic Polyol R-1 are particularly preferred.

The Pluronic and Butronic nonionic surface-active agents have been found to minimize the astringency of the zinc chloride and can be present in the amount of from about 0.5 to 10%, preferably about 1.0 to 5.0%.

Other nonionic surface-active agents which may be employed are the condensates of sorbitan monostearate with approximately 20 moles of ethylene oxide. Amphoteric agents include the quaternized imidazole derivatives which are available under the tradename "Miranol" such as Miranol C$_2$M, from the Miranol Chemical Company.

Cationic surface-active agents can also be used. These compounds have detergent properties as well as germicidal and antibacterial properties. Examples of suitable cationic detergents are benzyl ammonium chloride, benzyl dimethyl stearylammonium chloride, tertiary amines having one fatty alkyl group of from 1–18 carbon atoms and two (poly)oxyethylene groups attached to the nitrogen and salts thereof with acids, and compounds of the structure:

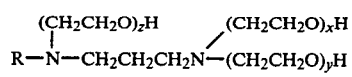

where R is a fatty alkyl group and can have from about 12 to 18 carbon atoms, and x, y, and z total 3 or higher, as well as salts thereof with mineral or organic acids, may also be used. About 0.5% to 15% by weight of these cationic surface-active agents can be used in dentifrice compositions.

In addition to the above described components, the dentifrices can contain a variety of optional conventional dentifrice ingredients. Such optional ingredients include preservatives, flavoring agents, sweetening agents, coloring agents and pigments.

Suitable flavoring agents include oil of wintergreen, oil of peppermint, oil of spearmint, oil of sassafras, and oil of clove. Sweetening agents which can be used include saccharin, dextrose, levulose, aspartame, D-tryptophan, dihydrochalcones and sodium cyclamate. Flavoring agents are generally utilized in dentifrices at levels of from about 0.01% to 2% by weight and sweetening agents at levels of from about 0.05% to about 2% by weight.

These dentifrice compositions are prepared by mixing together the components by conventional means. Once prepared, the compositions have a pH of from about 3.5 to 6.0, when said compositions are slurried with water in a 3:1 weight ratio of water to composition. These dentifrice compositions are used in conventional manner, i.e., the compositions or slurries are brushed onto dental surfaces and subsequently rinsed away. During use of the dentifrices in this manner, pastes or slurries generally contact dental surfaces for at least about 30 seconds. More preferably, such pastes or slurries contact dental surfaces for at least about 60 seconds.

While the previous discussions have been directed to dentifrice compositions, the present invention may also encompass compositions in the form of a mouthwash, gel, powder, solution, varnish, lozenge, chewing gum, slow release device or other form suitable for oral application. Any pharmaceutically acceptable material, such as those ordinarily used in such oral compositions, that are compatible with the zinc and fluoride ions may be employed in the compositions of this invention.

Specific embodiments of the present invention are illustrated by the following representative examples. It will be understood, however, that the invention is not confined to the specific limitations set forth in the individual examples but rather to the scope of the appended claims.

All percentages used herein are by weight unless otherwise designated.

EXAMPLE I

An opacified dentifrice having the following composition is formulated:

|  | % w/w |
|---|---|
| sodium fluoride | 0.22 |
| zinc chloride | 2.00 |
| sorbitol (70% aqueous) | 35.00 |
| glycerin | 10.00 |
| hydrated silica | 23.00 |
| sodium methyl cocoyl taurate | 3.75 |
| xanthan gum | 1.00 |
| hydroxyethylcellulose | 1.00 |
| sodium gluconate | 0.80 |
| titanium dioxide | 0.80 |
| sodium saccharin | 0.70 |
| saccharin | 0.10 |
| sodium benzoate | 0.20 |
| flavor | 1.30 |
| deionized water q.s. to | 100.00 |

EXAMPLE II

Another opacified dentifrice having the following composition is formulated:

|  | % w/w |
|---|---|
| sodium fluoride | 0.22 |
| zinc chloride | 2.00 |
| sorbitol (70% aqueous) | 35.00 |
| glycerin | 10.00 |
| hydrated silica | 23.00 |
| Pluronic F-85 (a tradename of Wyandotte Corp. for conjugated polyoxyethylenes-polyoxypropylenes) | 3.00 |
| xanthan gum | 1.00 |
| hydroxyethylcellulose | 1.00 |
| titanium dioxide | 0.80 |
| sodium gluconate | 0.80 |
| sodium saccharin | 0.70 |
| saccharin | 0.10 |
| sodium benzoate | 0.20 |
| flavor | 1.30 |
| deionized water q.s. to | 100.00 |

EXAMPLE III

Another opacified dentifrice having the following composition is formulated:

|  | % w/w |
|---|---|
| sodium fluoride | 0.22 |
| zinc chloride | 0.50 |
| sorbitol (70% aqueous) | 40.00 |
| glycerin | 15.00 |
| hydrated silica | 23.00 |
| polyethylene glycol | 5.00 |
| sodium methyl cocoyl taurate | 3.75 |
| xanthan gum | 0.50 |
| hydroxyethylcellulose | 0.50 |
| sodium saccharin | 0.50 |
| saccharin | 0.30 |
| sodium gluconate | 0.27 |
| sodium benzoate | 0.20 |
| titanium dioxide | 0.20 |
| flavor | 1.00 |
| deionized water q.s. to | 100.00 |

EXAMPLE IV

A gel dentrifice having the following composition is formulated:

|  | % w/w |
| --- | --- |
| sodium fluoride | 0.22 |
| zinc chloride | 0.50 |
| sorbitol (70% aqueous) | 50.00 |
| glycerin | 5.00 |
| hydrated silica | 23.00 |
| polyethylene glycol | 5.00 |
| sodium methyl cocoyl taurate | 3.75 |
| xanthan gum | 0.50 |
| hydroxyethylcellulose | 0.50 |
| sodium gluconate | 0.27 |
| sodium saccharin | 0.50 |
| saccharin | 0.15 |
| sodium benzoate | 0.20 |
| flavor and coloring agents | 0.70 |
| deionized water q.s. to | 100.00 |

EXAMPLE V

Comparative studies were conducted on rats utilizing the composition described in Example III, a commercial dentifrice (Oentifrice A) containing 0.5% zinc citrate, 0.8% sodium monofluorophosphate, having a pH of 7.85 and no buffer system, as well as another commercial dentifrice (Dentifrice B) which contains no zinc chloride, 0.22% sodium fluoride, a phosphate buffer, and has a pH of 7.05. In these studies, each group consisted of thirty male Wistar rats, approximately 50 grams each and caged by pairs in raised wire cages. At nineteen days of age the animals were weighed and randomly distributed into groups. The animals were fed NIDR Diet No. 5000 and were given deionized water to drink ad libitum. Approximately 0.15 of each preparation was applied with a cotton applicator per jaw. Treatments were applied twice per day, seven days per week, for three weeks. Immediately prior to sacrifice, all animals were observed for any visual signs of ill health and individually weighed. At the end of three weeks, the animals were sacrificed; the heads cleaned, the jaws and teeth sectioned, stained and scored for dental caries by the Keyes Method. The data were then analyzed for significant differences between means, for both the number and seVerity of carious lesions. The results are shown in Table I below:

TABLE I
Rat Caries Studies

| Formula | % Zinc Salt | Sodium Gluconate Buffer | pH | % Fluoride Salt | % Red. in Number Enamel Lesions | % Red. Severity Enamel Lesions |
| --- | --- | --- | --- | --- | --- | --- |
| Example III | 0.5% ZnCl$_2$ | Yes | 4.75 | 0.21% NaF | 26.0 | 27.0 |
| Dentifrice A | 0.5% Zinc Citrate | No | 7.85 | 0.8% NaMFP | 9.0 | 5.0 |
| Dentifrice B | None | No | 7.1 | 0.21% NaF | 1.0 | 6.0 |

These results above clearly show that the composition of Example III is significantly superior to the two commercial formulations in reducing both the number and severity of dental lesions.

EXAMPLE VI

Solutions each contain 35.00 g. sorbitol. 10.0 g. glycerol, 2.00 g. zinc chloride, 0.22 g. sodium fluoride and 16.00 g. deionized water are prepared. To each of these solutions various organic acids and salts are added in varying amounts and mixed resulting in clear solutions within the desired pH range. The solutions are left for one week at 60° C. and then reviewed and noted as either clear, hazy or exhibiting a precipitate. The results are shown below in Table II:

TABLE II

| Organic Acid/Salt | conc. (gm.) | pH (init.) | One Week Aging |
| --- | --- | --- | --- |
| (No organic acid/salt) | 0 | 5.50 | precipitate |
| adipic acid | 0.10 | 4.00 | precipitate |
| glucuronic acid | 0.10 | 4.45 | clear |
| fumaric acid | 0.10 | 4.35 | clear |
| malic acid | 0.10 | 4.40 | haze |
| lactic acid | 0.10 | 4.65 | precipitate |
| aspartic acid | 0.10 | 4.85 | clear |
| succinic acid | 0.10 | 4.65 | clear |
| tartaric acid | 0.10 | 4.60 | precipitate |
| maleic acid | 0.10 | 4.60 | clear |
| glucuronic acid lactone | 0.10 | 4.85 | clear |
| gluconic acid (50%) | 0.20 | 4.00 | clear |
| sodium gluconate | 0.80 | 5.35 | clear |
| sodium glutamate | 0.10 | 4.85 | clear |

The above results demonstrate that without any organic acid/salt a precipitate is formed. However, not all organic acids are useful in the compositions of the present invention. Those acids that result in the formation of a precipitate or haze (start of precipitate) would not be useful since they would result in a reduction in the available fluoride ions and zinc ions.

EXAMPLE VII

A tooth powder composition is prepared according to conventional means containing the following ingredients:

|  | % w/w |
| --- | --- |
| silica hydrogel | 96.21 |
| zinc chloride | 0.50 |
| sodium flouride | 0.22 |
| sodium gluconate | 0.27 |
| synthetic sweetener (saccharin, aspartame) | 0.50 |
| sodium methylcocoyltaurate | 1.50 |
| flavoring | 0.80 |

EXAMPLE VIII

An oral hygiene spray is prepared according to conventional means containing the following ingredients:

|  | % w/w |
| --- | --- |
| ethanol | 15.00 |
| zinc chloride | 0.50 |
| sodium fluoride | 0.05 |
| sodium gluconate | 0.27 |
| saccharin | 0.50 |
| flavoring | 1.00 |
| propellant | 5.00 |

-continued

|  | % w/w |
| --- | --- |
| deionized water q.s. to | 100.00 |

EXAMPLE IX

A mouthrinse composition is prepared according to conventional means containing the following ingredients:

|  | % w/w |
| --- | --- |
| ethyl alcohol (190 proof) | 6.00 |
| Pluronic F-127 | 1.75 |
| zinc chloride | 0.25 |
| sodium fluoride | 0.05 |
| sodium gluconate | 0.15 |
| glycerin | 8.00 |
| sodium saccharin | 0.25 |
| saccharin | 0.30 |
| cetylpyridinium chloride | 0.10 |
| flavoring and color | 2.50 |
| deionized water q.s. to | 100.00 |

EXAMPLE X

A lozenge composition is prepared according to conventional means containing the following ingredients:

|  | % w/w |
| --- | --- |
| sorbitol powder | 74.63 |
| corn syrup | 15.00 |
| zinc chloride | 0.50 |
| sodium fluoride | 0.22 |
| flavor and color | 1.15 |
| sodium gluconate | 0.30 |
| synthetic sweeteners | 0.20 |
| tableting lubricant | 5.00 |
| deionized water | 3.00 |

EXAMPLE XI

A chewing gum composition is prepared according to conventional means containing the following ingredients:

|  | % w/w |
| --- | --- |
| gum base | 30.00 |
| sorbitol | 48.98 |
| corn syrup | 15.00 |
| flavor | 1.50 |
| zinc chloride | 0.50 |
| sodium fluoride | 0.22 |
| sodium gluconate | 0.30 |
| gum tragancanth | 0.50 |
| deionized water | 3.00 |

What is claimed is:

1. An oral hygiene composition consisting essentially of an effective concentration of a pharmaceutically acceptable fluoride salt selected from the group consisting of sodium fluoride, potassium fluoride, lithium fluoride, aluminum fluoride, zinc fluoride, stannous fluoride, sodium monofluorophosphate, acidulated phosphate fluoride, ammonium fluoride, ammonium bifluoride, titanium tetrafluoride and amine fluoride, a pharmaceutically acceptable zinc salt selected from the group consisting of zinc chloride, zinc sulfate and zinc thiocyanate, a buffering agent selected from the group consisting of sodium gluconate, maleic acid, aspartic acid, gluconic acid, succinic acid, glucuronic acid, glucuronic acid lactone, fumaric acid and sodium glutamate and a suitable oral hygiene vehicle and having a pH of from about 3.5 to 6.0.

2. The composition of claim 1 wherein the fluoride ion is present in a concentration of from about 0.0025 to about 4.0% by weight.

3. The composition of claim 2 wherein the fluoride ion concentration is in the range of from about 0.005 to about 1.0 by weight.

4. The composition of claim 2 wherein the fluoride ion concentration is in the range of from about 0.02 to about 0.5% by weight.

5. The composition of claim 2 wherein the zinc ion is present in a concentration of from about 0.02 to about 30.0% by weight.

6. The composition of claim 5 wherein the zinc ion concentration is from about 0.05 to about 10.0% by weight.

7. The composition of claim 6 wherein the zinc ion concentration is from about 0.1 to about 5.0% by weight.

8. The composition of claim 1 wherein the buffering agent is present in a concentration of from about 0.01 to about 10.0% by weight.

9. The composition of claim 8 wherein the buffering agent concentration is from about 0.05 to about 5.0% by weight.

10. The composition of claim 1 wherein the buffering agent is sodium gluconate.

11. The composition of claim 1 wherein the vehicle comprises at least one member selected from the group consisting of glycerol, water, ethanol, polyethylene glycol, propylene glycol and sorbitol.

* * * * *